United States Patent [19]

Wiederkehr

[11] Patent Number: 4,712,770
[45] Date of Patent: Dec. 15, 1987

[54] ELECTRICAL TENSIONING DEVICE FOR ORTHOPEDIC ADJUSTMENT MEANS

[76] Inventor: Hans Wiederkehr, Ifangstrasse 107, Rümlang, Switzerland

[21] Appl. No.: 728,207

[22] Filed: Apr. 29, 1985

[30] Foreign Application Priority Data

Apr. 30, 1984 [CH] Switzerland .................. 2106/84

[51] Int. Cl.⁴ ............................................. B66F 3/08
[52] U.S. Cl. ...................... 254/98; 254/103; 254/DIG. 2
[58] Field of Search ............. 254/98, 100, 102–103, 254/DIG. 2, DIG. 4; 128/69, 75

[56] References Cited

U.S. PATENT DOCUMENTS

| | | | |
|---|---|---|---|
| 959,157 | 5/1910 | Noyes | 254/98 |
| 1,600,597 | 9/1926 | Menges | 254/100 |
| 1,859,054 | 5/1932 | Runyon | 254/102 |
| 1,948,600 | 2/1934 | Templeton | 254/98 X |
| 2,283,476 | 5/1942 | Waibel | 254/103 X |
| 2,307,317 | 1/1943 | König | 254/103 X |
| 2,320,953 | 6/1943 | Shenstone | 254/98 |
| 2,482,464 | 9/1949 | Chapman | 254/103 X |
| 3,244,401 | 4/1966 | Iimura | 254/103 |
| 3,458,173 | 7/1969 | Kornovich et al. | 254/103 X |

FOREIGN PATENT DOCUMENTS 572684 10/1945 United Kingdom ................ 254/103

Primary Examiner—Frederick R. Schmidt
Assistant Examiner—Judy J. Hartman
Attorney, Agent, or Firm—Bachman & LaPointe

[57] ABSTRACT

A tensioning device has a worm gear mounted in a hollow section enabling the longitudinal displacement of a lift member with respect to a hollow section. The hollow section base and the lift member in each case carry a joint bolt, which cooperates with joint heads fixed to the adjustment means. The worm gear permits a very sensitive and exact setting of the spacing between the two joint bolts, which remains unchanged over a long period. In addition, the tensioning device is particularly suitable for orthopedic purposes, due to its small constructional volume.

7 Claims, 8 Drawing Figures

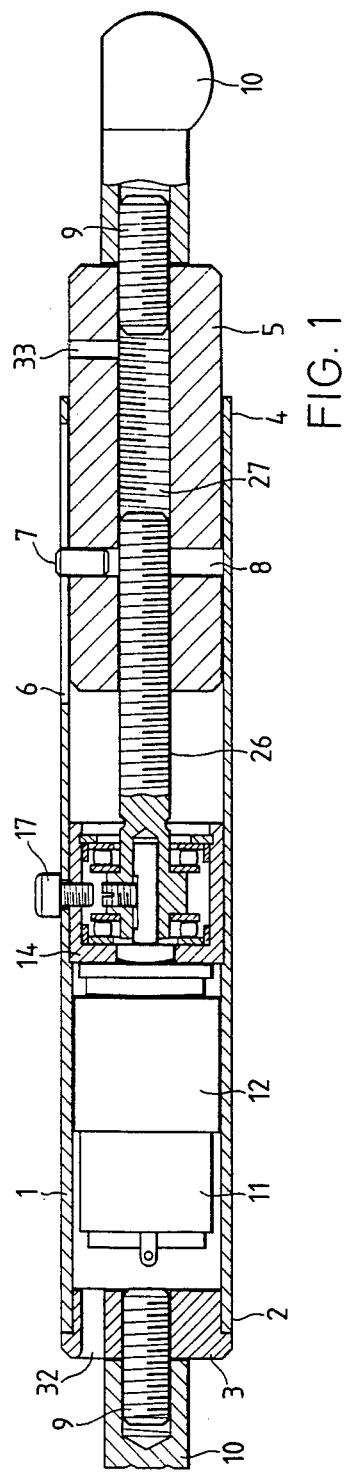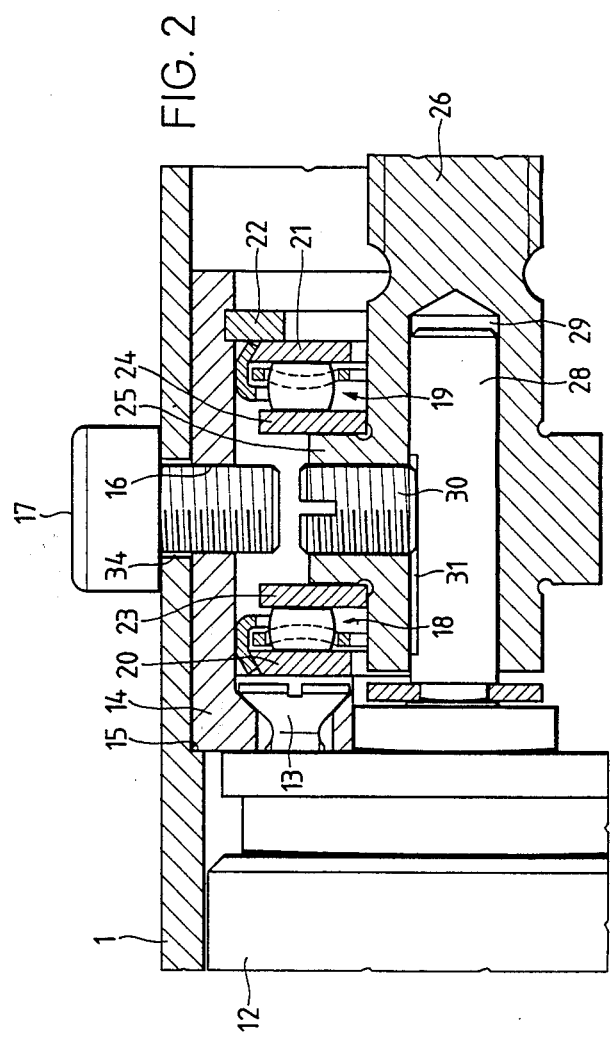

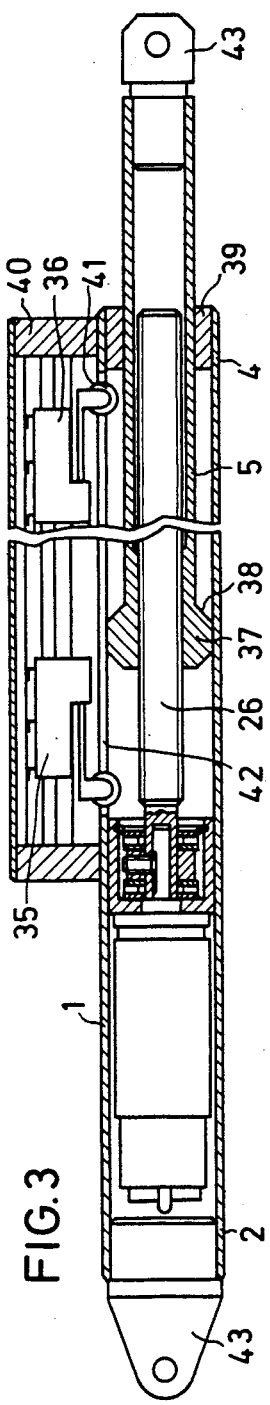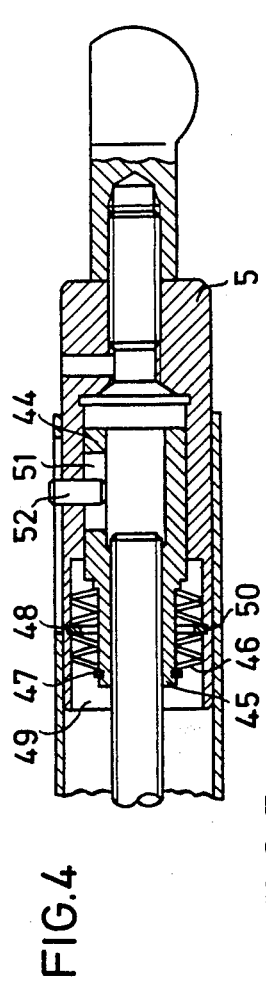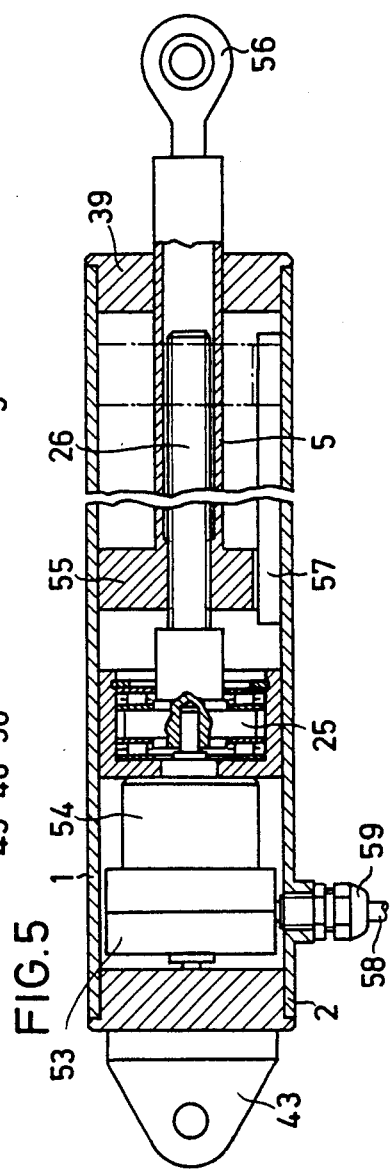

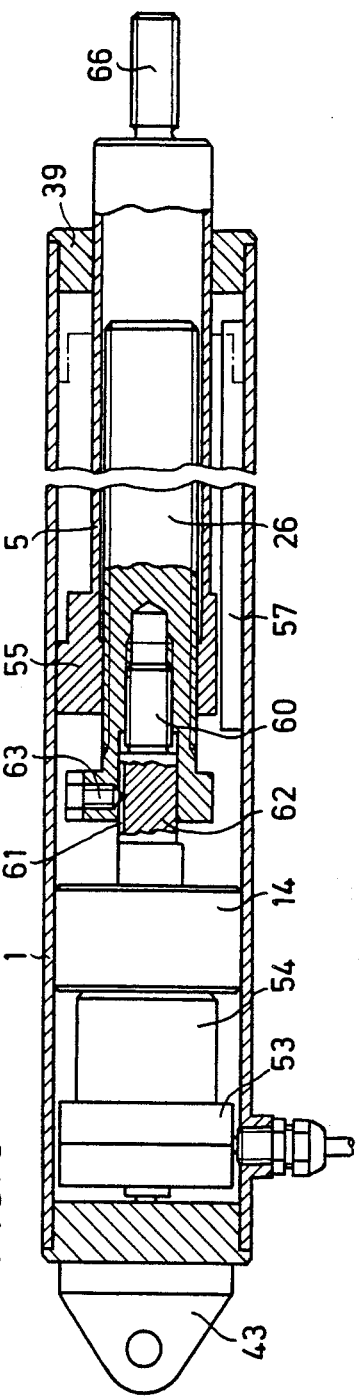

4,712,770

ELECTRICAL TENSIONING DEVICE FOR ORTHOPEDIC ADJUSTMENT MEANS

BACKGROUND OF THE INVENTION

The present invention relates to an electrical tensioning device for orthopedic adjustment.

In the case of wearers of orthopedic means, such as a support corset for the relief of the vertebral column when there are slipped disk problems, pains which occur can be admittedly soothed by administration of analgesics, but this is very unsatisfactory as a result of the disadvantages associated therewith. Therefore other means are being sought, including exerting forces on adjustment means, that is for modifying the tensioning action of a support corset, but such known means have not proved very satisfactory.

SUMMARY OF THE INVENTION

The object of the present invention is therefore to so develop a tensioning device of the aforementioned type that, on the one hand, a very limited constructional volume can be maintained and, on the other hand, a very accurate length setting of the tensioning device can be achieved. The foregoing object is achieved by way of the present invention.

BRIEF DESCRIPTION OF THE DRAWINGS

The invention is described in greater detail hereinafter relative to non-limitative embodiments and the attached drawings, wherein:

FIG. 1 is a longitudinal section through a tensioning device.

FIG. 2 is the area of the axial bearing of the worm gear of the tensioning device according to FIG. 1.

FIG. 3 is a longitudinal section through a second tensioning device with a lift setting.

FIG. 4 is a longitudinal section through a tensioning device according to FIG. 1 with a flexible guide bush.

FIG. 5 is a longitudinal section through a third tensioning device with stepping motor and position indicator.

FIG. 6 is a longitudinal section through a fourth tensioning device with stepping motor and geared down double spindle.

FIG. 7 is a longitudinal section through a fifth tensioning device with stepping motor and ball threaded spindle.

DETAILED DESCRIPTION

Figure 8:
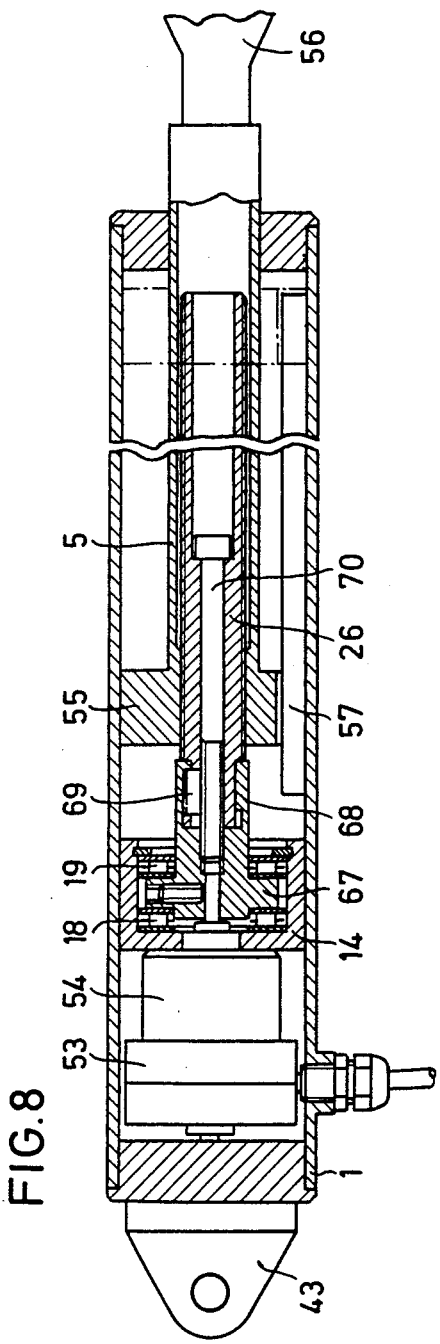
FIG. 8 is a longitudinal section through a sixth tensioning device with an interchangeable threaded spindle.

The invention is based on the idea that adjustment devices for orthopedic purposes are only completely satisfactory from the patient's standpoint, if a position chosen on the device remains unchanged for a long period, that is, several hours, while at the same time an extremely accurate and sensitive setting of the device is necessary. The foregoing is made possible by the hereinafter described embodiments of the present invention.

The tensioning device according to FIG. 1 has a hollow section or housing 1, which has a substantially constant diameter along its length and is terminated at one end by a base 3; however, the latter can be omitted, which facilitates disassemblability of the parts arranged in the interior of hollow section 1. The other end 4 of hollow section 1 is open and forms the guide for a lift member 5, which is longitudinally displaceably guided in hollow section 1. For guiding the lift member 5 a longitudinal slot 6 is provided in hollow section 1, into which projects a bolt 7, such as a cotter pin, which is mounted in a radial bore 8 of lift member 5. A threaded bolt 9 is screwed into base 3 and on its projecting end is screwed a joint bolt 10 which is only partially illustrated. On the opposite side of hollow section 1, an identical threaded bolt 9 with a joint bolt 10 is screwed into lift member 5 on one end face thereof. The joint bolt 10 is part of an angle joint, whose counterpart is fixed in the adjusting device and terminates in a joint head, on which is supported a ball cap arranged at one end of joint bolt 10. For the other facing joint bolt 10 is supported a further joint head, which is also in the adjusting device.

In hollow section 1 is housed a low voltage electric motor 11 with a reduction gear 12, the latter being supported by means of screws, such as countersunk screws 13 (FIG. 2) on a bearing bush 14. The latter is inserted in hollow section 1 and its position is defined by a shoulder 15 therein. Within the bearing bush 14 is provided a taphole 16, into which is screwed a screw 17 projecting from the outside through a bore 34 in hollow section 1 and fixes bearing bush 14 in position.

Within the bearing bush 14 are arranged two axial antifriction bearings 18, 19, such as axial needle bearings, whose bearing rings 20, 21 are supported on the bottom of bearing bush 14 or on a circlip 22 mounted within bush 14, while the corresponding counterrings 23, 24 engage with a flange 25 forming part of spindle 26. Spindle 26 is screwed on one side into lift member 5, which forms with its taphole 27 the nut of a worm gear, whose spindle is spindle 26. Reduction gear 12 connected to electric motor 11 has a gear shaft 28. The end of spindle 26 with bore 29 is placed on gear shaft 28. A securing means in the form of a spigot 30 is screwed into flange 25 and its end face projects into a groove 31 formed in gear shaft 28 and ensures the drive between gear shaft 28 and spindle 26. As can be gathered from FIG. 2, after removing screws 17, spigot 30 can be loosened or tightened, so that the connection between gear shaft 28 and spindle 26 can be loosened or tightened.

Base 3 has a bore 32, through which can be drawn an electric cable and this enables a connection to be formed between the electric motor 11 and a power source, such as a battery. A further bore 33 in lift member 5 is used for venting the taphole 27 of the latter.

If base 3 is omitted to bring about better accessibility to the parts arranged within the hollow section 1, joint bolt 10 can be pivotably mounted on two pins on opposite sides of hollow section 1. In addition, the articulated pipe can be replaced by other connecting means, such as cover plates or spigots, which are connected with corresponding connection parts on the adjusting device or on the support means. The special arrangement of the parts makes it possible to easily fit and dismantle the aforementioned tensioning device. Firstly bolt 7 must be driven into the lift member 5 and the latter can then be unscrewed. After removing screw 17, spigot 30 can be loosened and then the bearing bush 14, reduction gear 12 and electric motor 11 can be removed together from the hollow section 1. The further disassembly takes place through removing the circlip 22, so that the spindle 26 can be released from the gear shaft 28. Assembly takes place in the same way, but in the reverse order.

By using this relatively narrow outer sleeve 2 it is possible to achieve a space-saving tensioning device and it is also possible to achieve very high speed reductions, that is of approximately 150:1. As a result of this high setting precision, it is possible to set the adjusting devices in such a way as to bring relief to the patient.

FIGS. 3 to 7 show embodiments of tensioning devices, such as can be used in orthopedic adjusting means, like that of FIG. 1, but which have additional elements. In FIGS. 3 to 7 reference numerals coinciding with those of FIG. 1 designate identical parts, which are only mentioned to illustrate the overall function.

The tensioning device according to FIG. 3 differs from that according to FIG. 1 through the attachment of displaceable limit switches 35, 36 which make it possible to adjust the stroke or lift of the worm gear. For this purpose, lift member 5 is constructed in the vicinity of the part forming the spindle nut as a head 37 with facets 38, on which run the feeler rolls of limit switches 35, 36. As in this case lift member 5 has a smaller diameter than the internal diameter of the hollow section and is consequently only defined therein in the vicinity of head 37, a guide ring 39 for guiding the smaller diameter lift member part is arranged at the other end 4.

Limit switches 35, 36 are fitted in a housing 40, which is fixed to the external diameter of the hollow section 1, such as by screwing. The housing or part thereof is removed for setting limit switches 35, 36. The feeler rolls 41 project through a slot 42 into the interior of hollow section 1. In addition, lift member 5 is provided in such a way that there can be no rotation of the lift member during the stroke or lift adjustment. In place of the joint bolt 5 at one end 2 and at the end of lift member 5 is in each case provided a cover plate 43 for the connection of the tensioning device to the other parts.

The tensioning device according to FIG. 4 substantially corresponds to those according to FIG. 1, but in this case spindle 26 is resiliently connected to the lift member 5. For this purpose a guide sleeve 44 is screwed onto spindle 26 and has a neck 45, on which is mounted a set of springs, such as cup springs, which are held together by a circlip 47. The central cup springs are held in a groove 50 of a bore 49 of lift member 5. The relative movement of lift member 5 with respect to guide sleeve 44 takes place within a slot 51, into which projects a bolt 52 mounted in lift member 5. As a result of the described spring mounting, the sudden transition from loading to relief and vice versa is damped.

FIG. 5 shows a tensioning device, where the electric motor is replaced by an electric stepping motor 53 with a reduction gear. The bearing arrangement is the same as in FIG. 2, but flange 25 is larger in view of the larger diameter of hollow section 1 resulting from the stepping motor 53. Lift member 5 has a guide head 55, which guides the lift member within the hollow section 1, while the smaller diameter part of lift member 5 is guided in guide ring 39. At the end of the guide head is provided a connecting ring 56, while a cover plate 53 acts as the connecting means at one end 2 of hollow section 1.

It is also important that a displacement transducer 57 arranged in the vicinity of guide member 5 within hollow section 1 is associated with stepping motor 53 and is used for regulating the position of lift member 5. The displacement transducer 57 is appropriately constructed as a digital displacement transducer. FIGS. 5, 6 and 7 also show the electric lead 58 with a coupling 59 for fixing the latter to hollow section 1.

In the case of the tensioning devices according to FIGS. 6 and 7, there is once again a stepping motor which acts as an electric drive. However, in the case of Figure 6, a double spindle is used, so that two speeds, namely a higher speed and a lower speed can be imparted to the lift member.

The double spindle arrangement has spindle 26 which, with the lift member 5, forms the worm gear corresponding to that of FIGS. 1, 3, 4 and 5. A further spindle 60 is screwed into the drive side end of spindle 26 and is connected to a drive part 62 having a groove 61 and which is in turn coupled to the drive shaft of reduction gear 54. A resilient catch 63 projects into groove 61 and is positioned at the drive side end of spindle 26. If the lift member 5 moves without loading, the force action of the catch 63 is adequate, so that no relative movement takes place between spindle 26 and spindle 60. If a force action occurs on lift member 5, the resilient or spring-mounted catch 63 snaps out of the groove 61. The resulting relative movement between spindles 26 and 60 leads to a lower speed of lift member 5. The tensioning device according to FIG. 6 is consequently able to work with two speeds, depending on whether little or no load or a high load acts on the lift member 5.

The tensioning device according to FIG. 7 has a worm gear with a ball thread spindle. A housing 64, which contains the balls and the necessary ball channels for the revolution of the balls, is screwed into a taphole 65 of guide head 55, while the spindle 26 is connected to the outlet shaft of reduction gear 54, as in the case of the tensioning devices according to FIGS. 1, 3, 4, and 5. The remaining parts of the tensioning device 7 correspond to those of FIG. 6. In the case of both tensioning devices, lift member 5 has a threaded bolt 66 at its end as a connecting means.

The tensioning device according to FIG. 8 is provided in the same way as that of FIG. 5 with an electric stepping motor 53 and a reduction gear 54. To the reduction gear is connected a bearing arrangement, which comprises bearing bush 14, the axial antifriction bearings 18, 19 and a bearing body 67 with a spindle connection 68. Spindle 26, which is constructed as a hollow spindle in FIG. 8, is mounted in non-rotary manner in spindle connection 68 by means of a key joint 69 and is secured by a screw bolt 70 screwed into the bearing body 67. The spindle nut of spindle 26 is the guide head 55 with the lift member 5 fixed thereto and whose free end carries a connecting ring 56. As in the embodiment according to FIGS. 5, 6 and 7, a displacement transducer 57 is fitted into the hollow section 1 and enables a displacement measurement to be carried out.

The advantage of the tensioning device according to FIG. 8 is that the set of spindles, that is spindle 26 and the guide member 55 of lift member 5 can be separated from the drive by loosening screw bolt 70 and can be rapidly and effortlessly replaced by another spindle arrangement.

In summarizing, the described tensioning devices are characterized by a simple and consequently inexpensive construction, with limited space requirements. Preferably the electromotive drive is operated with low voltage, but a construction for mains voltage is also possible. The fundamental construction of the tensioning device leads to numerous advantages, such as simple attachment of limit switches, simple fitting of a spring mounting system between lift member 5 and spindle 26, as well as a simple transfer to stepping motors, optionally combined with displacement transducers 57 for providing a control loop.

The bearing arrangement of FIGS. 1, 2, 3, 5 and 8 have antifriction bearing, but it is also possible to use other bearing arrangements, such as with friction bearings or friction and antifriction bearings.

The aforementioned tensioning devices have numerous applications in the orthopedic field, such as exerting a force on a support corset, actuating artificial limbs and as movement aids. However, the possible uses are not limited to the orthopedic field and in fact they can be used wherever the special characteristics thereof can be appropriately employed.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed is:

1. An orthopedic tensioning device comprising a hollow elongated housing having a slot therein; a lift member guidably mounted in said housing at one end thereof for reciprocal movement therein, said lift member having guide means receivable in said slot in said housing so as to prohibit said lift member from rotating while guiding said lift member for reciprocal movement; motor means mounted in said housing at the other end thereof for driving said lift member, said motor means comprising an electric motor, a gear reduction means connected to said electric motor and an output shaft from said gear reduction means; transmission means between said output shaft and said lift member, said transmission means including a worm gear comprising a threaded spindle having one end threadably received in a bore provided in said lift member and the other end connected to said output shaft of said gear reduction means; and bearing means provided in said housing between said electric motor and said worm gear about said output shaft for absorbing oppositely acting axial forces, said bearing means being situated in a bushing fitted on the inner wall of said housing including means external of said housing engaging with said bushing for releasably securing said bearing means in said housing.

2. A tensioning device according to claim 1 including means internal of said housing for releasably securing said spindle to said output shaft.

3. A tensioning device according to claim 1 including a displacement transducer arranged within the housing and associated with said lift member.

4. A tensioning device according to claim 1 wherein a further spindle is screwed into the spindle of the worm gear and is connected to a drive part having a drive groove into which projects a resilient catch mounted in the drive side end of the first spindle, for the purpose of the rigid coupling of the two spindles until a spindle loading limit is reached at a first advance speed and for introducing a relative movement between the spindle after releasing the catch on exceeding the spindle loading limit at a second advance speed, which is lower than the first advance speed.

5. The tensioning member according to claim 1 wherein said housing has a substantially constant diameter along its length.

6. The tensioning device according to claim 1 including means internal of said housing for releasably securing said spindle to said output shaft, and said external securing means and said internal securing means being substantially axially aligned.

7. An orthopedic tensioning device comprising a hollow elongated housing having a slot therein; a lift member guidably mounted in said housing at one end thereof for reciprocal movement therein, said lift member having guide means receivable in said slot in said housing so as to prohibit said lift member from rotating while guiding said lift member for reciprocal movement; motor means mounted in said housing at the other end thereof for driving said lift member, said motor means comprising an electric motor, a gear reduction means connected to said electric motor and an output shaft from said gear reduction means; transmission means between said output shaft and said lift member, said transmission means including a worm gear comprising a threaded spindle having one end threadably received in a bore provided in a guide sleeve in said lift member and the other end connected to said output shaft of said gear reduction means; spring means for resiliently mounting said guided sleeve in a bore in the lift member; and bearing means provided in said housing between said electric motor and said worm gear about said output shaft for absorbing oppositely acting axial forces, said bearing means being situated in a bushing fitted on the inner wall of said housing, including means external of said housing engaging with said bushing for releasably securing said bearing means in said housing.

* * * * *